(12) United States Patent
Flohr et al.

(10) Patent No.: US 6,236,707 B1
(45) Date of Patent: May 22, 2001

(54) METHOD FOR THE RECONSTRUCTION OF IMAGES FROM MEASURED VALUES ACQUIRED WITH A CT APPARATUS BY SPIRAL SCAN OF THE EXAMINATION SUBJECT AND CT APPARATUS FOR THE IMPLEMENTATION OF THE METHOD

(75) Inventors: Thomas Flohr, Uehlfeld; Stefan Schaller, Fuerth, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/352,447

(22) Filed: Jul. 13, 1999

(30) Foreign Application Priority Data

Jul. 17, 1998 (DE) .............................................. 198 32 275

(51) Int. Cl.[7] ...................................................... A61B 6/03
(52) U.S. Cl. ............................................... 378/15; 378/901
(58) Field of Search ................................. 378/4, 15, 901

(56) References Cited

U.S. PATENT DOCUMENTS

| | | | |
|---|---|---|---|
| 5,539,796 | 7/1996 | Takagi et al. | 378/20 |
| 5,559,847 | 9/1996 | Hu et al. | 378/4 |
| 5,825,842 * | 10/1998 | Taguchi | 378/15 |
| 6,140,775 * | 8/2000 | Tuy | 378/4 |

FOREIGN PATENT DOCUMENTS 0 713 678    5/1996   (EP) .

* cited by examiner

*Primary Examiner*—David V. Bruce
(74) *Attorney, Agent, or Firm*—Schiff Hardin & Waite

(57) ABSTRACT

In method and apparatus for the reconstruction of images of a slice of an examination subject having a slice thickness with respect to an image plane from measured values acquired by a spiral scan of the examination subject with an x-ray source rotating around the examination subject with a detector having at least one line of detector elements, measured values lying within a maximum distance from the image plane are thereby involved in the reconstruction and are weighted such that a desired functional dependency of the slice thickness on the pitch is present.

6 Claims, 7 Drawing Sheets

METHOD FOR THE RECONSTRUCTION OF IMAGES FROM MEASURED VALUES ACQUIRED WITH A CT APPARATUS BY SPIRAL SCAN OF THE EXAMINATION SUBJECT AND CT APPARATUS FOR THE IMPLEMENTATION OF THE METHOD

BACKGROUND OF THE INVENTION

1. Field of the Invention

The present invention is directed to a method and computed tomography apparatus for reconstructing an image from measured values acquired by conducting a spiral scan of an examination subject.

2. Description of the Prior Art

Methods are known for the reconstruction of images of a slice of an examination subject having a slice thickness with respect to an image plane from measured values acquired with a CT apparatus by conducting a spiral scan of the examination subject with an x-ray source rotating around the examination subject and a detector formed by at least one line of detector elements. In such known methods, measured values are respectively allocated to different projection angles α and to a z-position on the longitudinal axis of the spiral scan, and a constant, dimensionless pitch p is adhered to during the spiral scan. This pitch p is defined as the ratio of the relative longitudinal shift (in mm) between (a) the examination subject, the x-ray source and the detector which occurs per full revolution of the x-ray source around the examination subject, and (b) the longitudinal width (in mm) of a line of the detector. "Longitudinal" means the direction of the longitudinal axis of the spiral scan. CT apparatuses for the implementation of such methods are also known.

Methods and CT apparatuses of this type are disclosed in U.S. Pat. No. 5,559,847, European Application 0 713 678, U.S. Pat. No. 5,539,796 and in Polacin et al., "Evaluation of Section Sensitivity Profiles and Image Noise in Spiral CT", Radiology, 1992, No. 185, pages 29 through 35.

In the reconstruction of images from measured values acquired by spiral scanning with a CT apparatus having a single-line detector, an interpolation between the measured values lying in front of and behind the image plane is implemented for each projection angle for generating calculated projections in the desired image plane.

Two interpolation methods are currently most standard: In the first, a linear interpolation is undertaken between respectively two measured projections lying closest to the image plane, these having been registered at the same projection angle a but in different revolutions. This type of interpolation is referred as 360LI interpolation. In the second method, an interpolation also is undertaken between two projections lying closest to the image plane, but one is registered at the projection angle $\alpha_d$ and the other is registered at the projection angle $\alpha_c$ complementary thereto ($\alpha_c = \alpha_d \pm \pi$ is valid for the middle detector element of the detector). This type of interpolation is referred to as 180LI interpolation. Given the same pitch, it supplies narrower effective layer widths (characterized, for example, by the full width at half maximum FWHM of the layer sensitivity profile) than the 360LI interpolation. Given the same output power (mA value) of the x-ray source, for example an x-ray tube, the pixel noise is increased in comparison to the 360LI interpolation as a tradeoff. The artifact susceptibility is also higher. Both interpolation types are illustrated schematically in FIG. 2 for the pitch p=2, with the projection angle α being shown as a function of the detector position in the z-direction. The projection angle α is entered on the longitudinal axis of the spiral scan (z-position) relative to the position normalized to the width b of a line of the detector.

All conventional interpolation methods for spiral scanning with a single-line detector have in common the fact that the width of the slice sensitivity profile (characterized, for example, by the full width at half maximum FWHM) increases with increasing pitch p. This is shown in FIG. 3 for the 180LI and the 360LI interpolation, which shows the full width at half maximum FWHM of the slice sensitivity profile referred to the collimated layer thickness $d_{coll}$ as a function of the pitch p. The relationship according to FIG. 3 complicates the procedure, particularly for unfamiliar users and represents a limitation in the selection of the examination parameters.

The situation becomes even less easily predictable when conventional interpolation techniques, for example the 360LI or 180LI interpolation, are employed for spiral scans implemented with a multi-line detector. FIG. 4 shows the full wave at half maximum FWHM of the slice sensitivity profile deriving in a 360LI and in a 180LI interpolation, again relative to the collimated slice thickness $d_{coll}$, as a function of the pitch p for a CT apparatus having a five-line detector. The full wave at half maximum now changes non-monotonously with the pitch. The relationship is not intuitive and is difficult to understand. Thus, for example, the full wave at half maximum FWHM can decrease given increasing pitch p.

SUMMARY OF THE INVENTION

An object of the present invention is to provide a method of the type initially described wherein a simplified operation of the CT apparatus is possible.

The above object is achieved in accordance with the principles of the present invention in an image reconstruction method, and in a computed tomography apparatus implementing the inventive image reconstruction method, wherein the image is an image of a slice of an examination subject having a slice thickness with respect to an image plane, wherein measured values are acquired in a computed tomography apparatus by conducting a spiral scan of the examination subject with an x-ray source and a radiation detector rotating around the examination subject, the detector having at least one line of detector elements, the measured values being respectively allocated to one of a number of projection angles α and to a z-position along the longitudinal axis of the spiral scan, while adhering to a constant, dimensionless pitch p during the spiral scan, the pitch p being defined as the ratio of the relative shift which occurs between the x-ray source and the detector and the patient during one full revolution of the x-ray source around the subject, with respect to the width of a line of the detector in the direction of the longitudinal axis of the spiral scan, and wherein, for each projection angle, all measured values belonging to this projection angle and lying within a maximum distance from the image plane are employed in the image reconstruction with the measured values being weighted according to a weighting function dependent on their spatial distance in the direction of a longitudinal axis from the image plane, with the weighting function being chosen so that a selectable, functionally defined relationship between the effective slice thickness and the pitch is present.

In the inventive method and apparatus, thus, the dependency of the effective slice thickness on the pitch p can be easily predicted (i.e., identified without resort to complicated calculations) since, differing from the prior art, there is no longer a more or less unpredictable relationship between the two that is defined by the interpolation method which is employed and which cannot be influenced except by the selection of the interpolation method. Instead, a selected functionally defined relationship is present. An inventive CT apparatus thus can be easily operated. This is particularly true when, in a version of the invention, the functional dependency is selected such that the effective slice thickness (the full wave at half maximum of the slice sensitivity profile, for example, can be utilized as criterion for this) is substantially independent of the pitch p.

A further simplification in operation is achieved in an embodiment of the invention, wherein the output power of the x-ray source is set dependent on the pitch p so that the pixel noise is substantially independent of the pitch p. It is then possible to set not only the slice sensitivity profile, but also the pixel noise, independently of the pitch p.

The setting of the desired slice thickness required in the invention ensues, according to one version of the invention, by varying the width of the weighting function, i.e. the maximum distance of the measured data to be taken into consideration from the image plane, dependent on the pitch p.

Since the inventive CT apparatus allows for setting an effective mAs product, from which an actual mAs product is set which produces pixel noise as would occur in an image acquired in a single-line detector with the same slice thickness given the effective mAs product, an operator is able to operate an inventive CT apparatus with a multi-line detector in a way that is just as simple as a CT apparatus having a single-line detector.

The basis for setting a slice sensitivity profile independently of the pitch p is a generalized weighting method instead of the standard interpolation. This weighting method, given a CT apparatus with M lines (M>1), allows setting of the slice sensitivity profile independently of the pitch p up to the maximum pitch $p_{max}=2$ M. As a result, the pitch p is no longer a parameter that determines the resolution in the z-direction. The physician can set the desired effective slice thickness and nonetheless freely select the pitch p.

DESCRIPTION OF THE PREFERRED EMBODIMENTS

Figure 1:
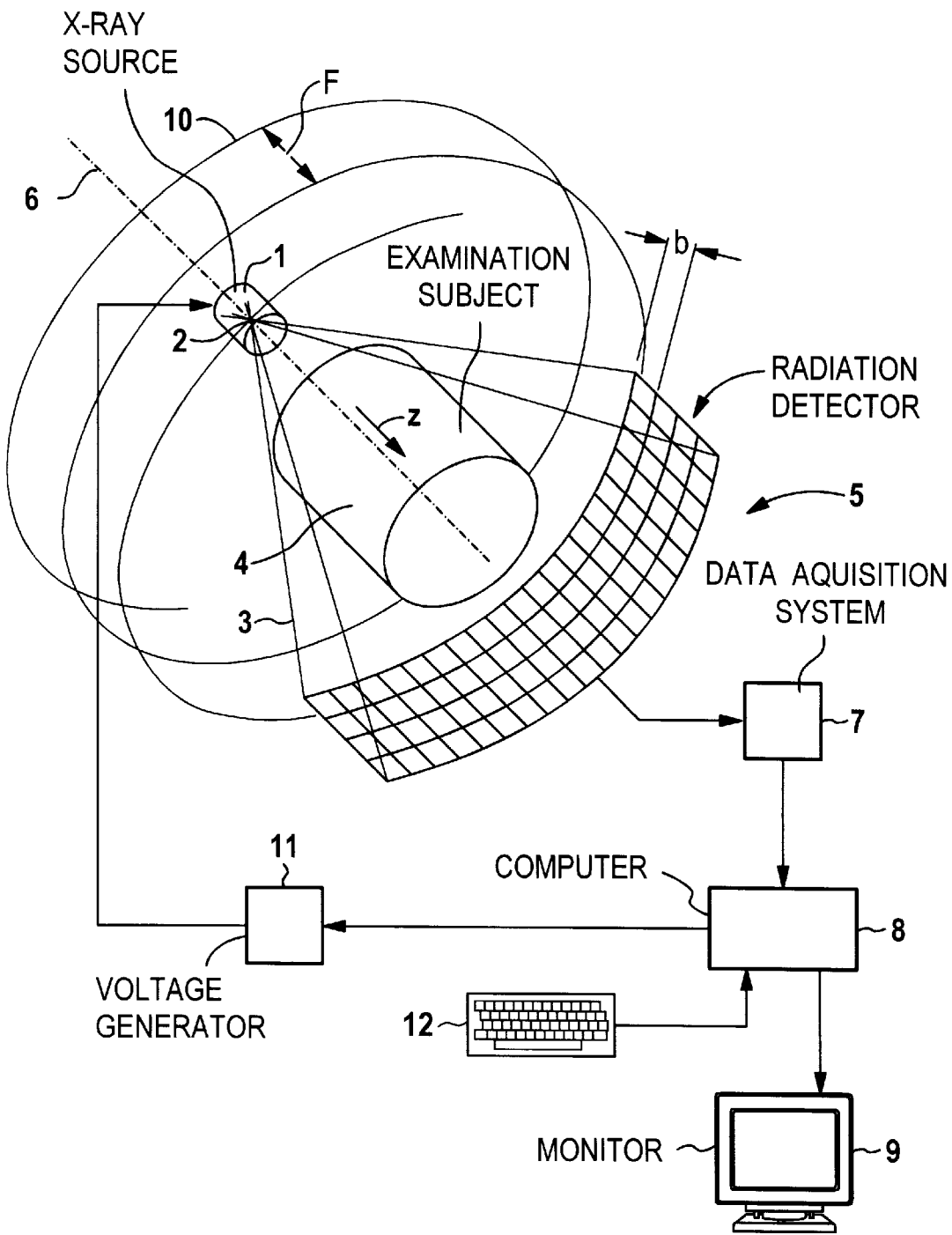
FIG. 1 is a schematic illustration of a CT apparatus constructed and operating in accordance with the invention.
Figure 2:
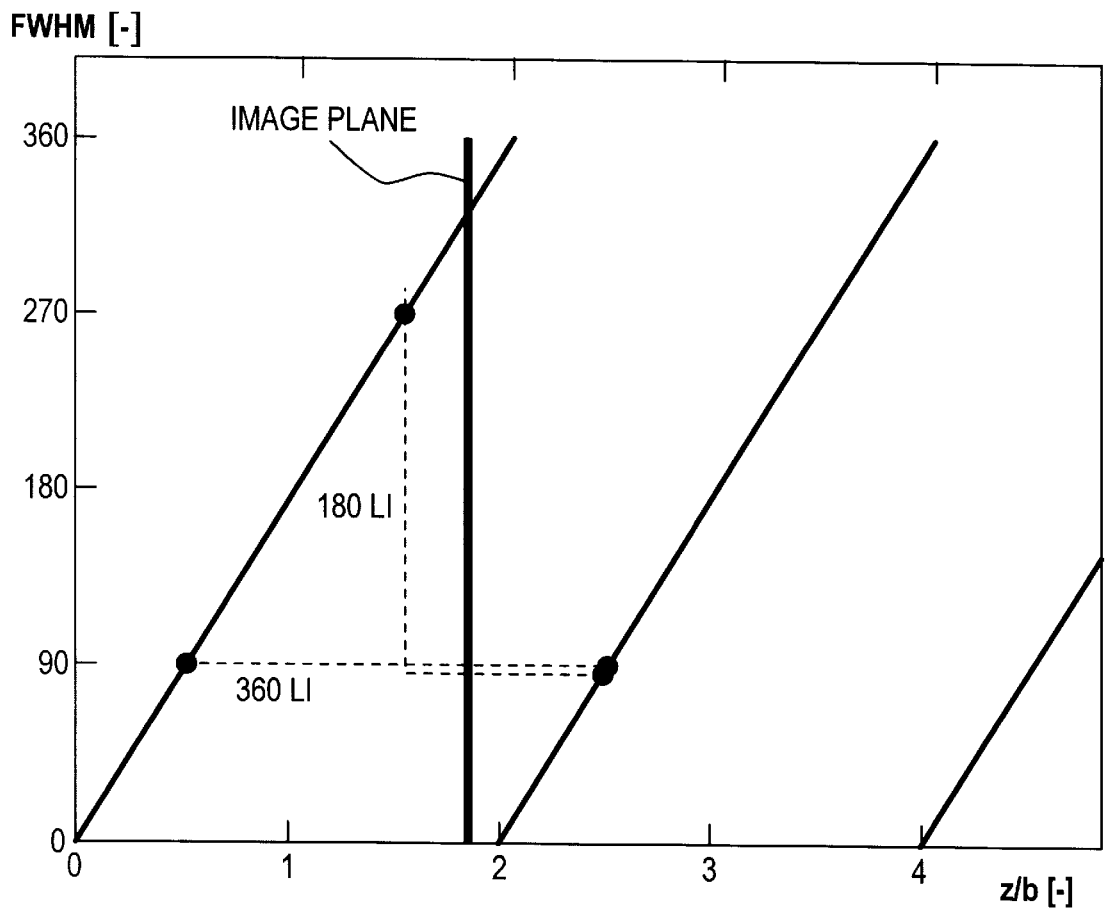
FIG. 2, as described above, is a diagram illustrating the interpolation methods which are standard in conventional reconstruction methods for a CT apparatus having a single-line detector.
Figure 3:
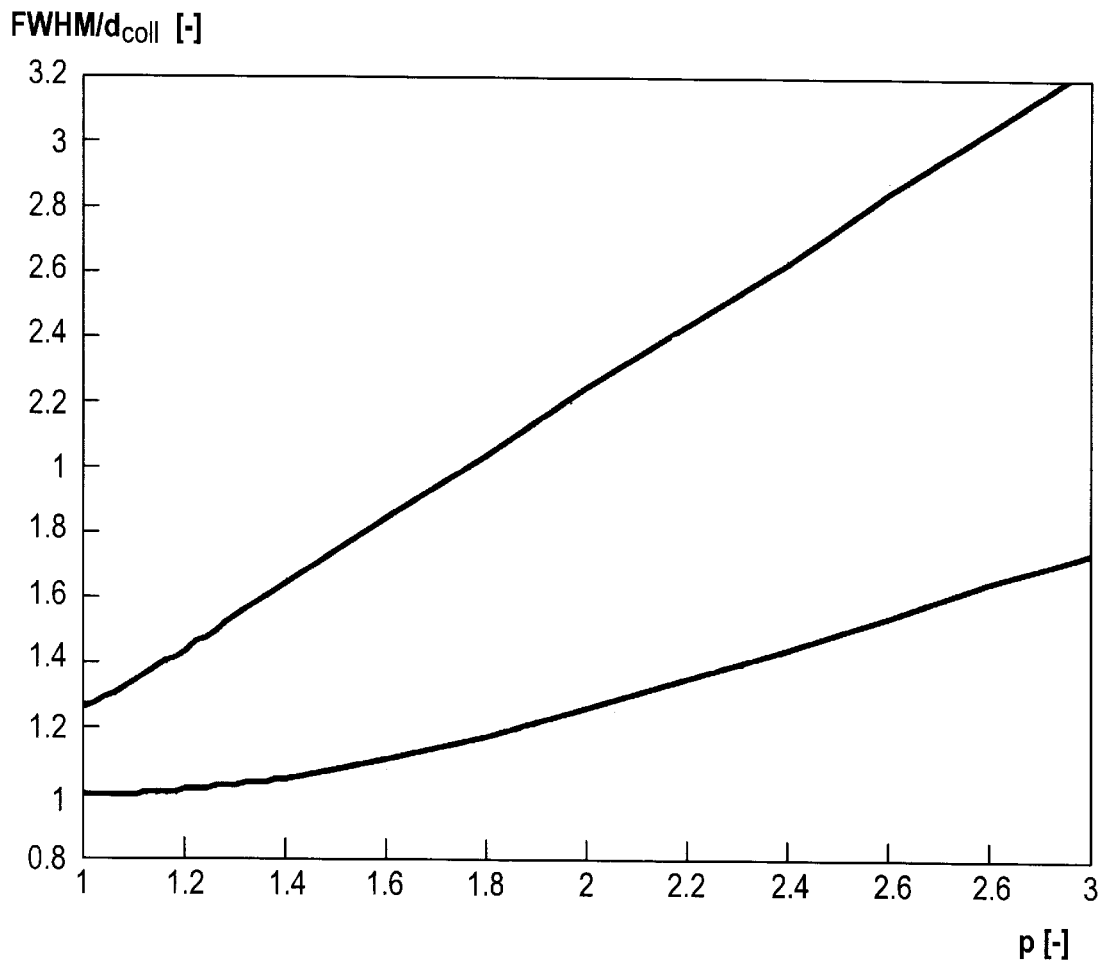
FIG. 3, as described above, shows the slice thickness for a conventional CT apparatus having a single-line detector with respect to the collimated slice thickness as function of the pitch.

In a schematic fashion, FIG. 1 shows a CT apparatus provided for the implementation of the inventive method that has an x-ray source 1, for example, an x-ray tube with a focus 2, from which a pyramidal x-ray beam 3 gated by a diaphragm (not shown) emanates. This beam 3 penetrates an examination subject 4, for example a patient, and is incident on a detector 5. The detector 5 is composed of a number of parallel detector lines, each formed by a row of detector elements. The x-ray source 1 and the detector 5 form a measuring system that is rotatable around a system axis 6, so that the examination subject 4 is trans-irradiated from different projection angles α. Using the output signals of the detector elements of the detector 5, a data acquisition system 7 forms measured values—referred to below as measured projections—that are supplied to a computer 8 which calculates an image of the examination subject 4 that is reproduced on a monitor 9.

Scanning larger volumes of the examination subject 4 is possible by the measuring system 1, 5 undertaking a spiral scan of the desired volume, as illustrated in FIG. 1 by a spiral 10. A relative movement between the measuring arrangement composed of the x-ray source 1 and the detector 5, and the examination subject 4, ensues in the direction of the system axis 6, which thus simultaneously represents the longitudinal axis of the spiral scan.

A keyboard 12 that enables the operation of the CT apparatus is connected to the computer 8, this simultaneously assuming the control of the CT apparatus in the described exemplary embodiment (it is also possible to provide a separate computer for this purpose).

In particular, it is possible to set the pitch p of the spiral scan via the keyboard 12. The pitch p is the quotient of the feed in the z-direction F occurring during a revolution of the measuring system and the width b of a line of the detector in the z-direction. The computer 8 also particularly serves the purpose of setting the tube current, and thus the output power, of the x-ray source 1 supplied by a voltage generator 11.

The transirradiation from different projection angles α is for acquiring different measured projections. To that end, the x-ray source 1 transirradiates the examination subject 4 with the x-ray beam 3 emanating from successive positions of the focus 2 lying on the spiral 10, each position of the focus 2 being allocated to a projection angle and to a z-position with respect to the system axis 6.

As a result of the spiral scan, at most one measured projection can exist with respect to an image plane proceeding at a right angle relative to the system axis 6, this projection having been registered with a position of the focus 2 lying in this image plane. In order nonetheless to be able to calculate an image of the slice of the examination subject 4 belonging to the respective image plane, thus, measured projections registered in the proximity of the image plane must be acquired by suitable interpolation methods, with each calculated projection in the case of measured projections being allocated to a projection angle a and to a z-position with respect to the system axis 6.

The inventive method is explained below with reference to the example of a CT apparatus having a five-line detector without this representing a limitation of the underlying principle. The applicability to other line numbers M≠5 will be apparent to those skilled in the field.

The calculation of an image for the position $z_{ima}$ of the image plane on the longitudinal axis of the spiral scan is described in detail below. The index ima stands for image.

The magnitudes of all measured values f (l, k, i, v) within a certain, selectable maximum distance $|z_{max}|$ from the image plane are taken into consideration for each projection angle $\alpha_l$. l=1, 2 ... $N_{p,\pi}$ is the projection number, with $N_{p,\pi}$ being the number of projections registered during half a revolution of the x-ray source 1, k is the detector channel, i=1, ... M is the number of the detector line and v is the number of the half revolution of the x-ray source 1 from which the appertaining projection derives.

All available measured values for each l are weighted according to their distance $\Delta z_{lkiv}$ from the image plane and $$p(l, k) = \frac{\sum_i \sum_v (\Delta z_{lkiv}) f(l, k, i, v)}{\sum_i \sum_v g(\Delta z_{lkiv})}$$

is obtained as resulting, calculated overall projection P(l,k). The function g( ) is the weighting function in the z-direction. Division by the sum of all weightings is necessary since a different number of measured values can contribute to each projection, but the total weighting, must be treated as one weighting.

Dependent on the pitch p, the width of the weighting function g( ), i.e. the maximum distance $|z_{max}|$ can be set such that the same effective slice sensitivity profile always occurs, for example characterized by the full wave at half maximum FWHM. The overall width of the weighting function needed for the respective value of the pitch p can be calculated by the computer 8 or can be taken from a table that is calculated in advance and stored in the computer 8.

Figure 5:
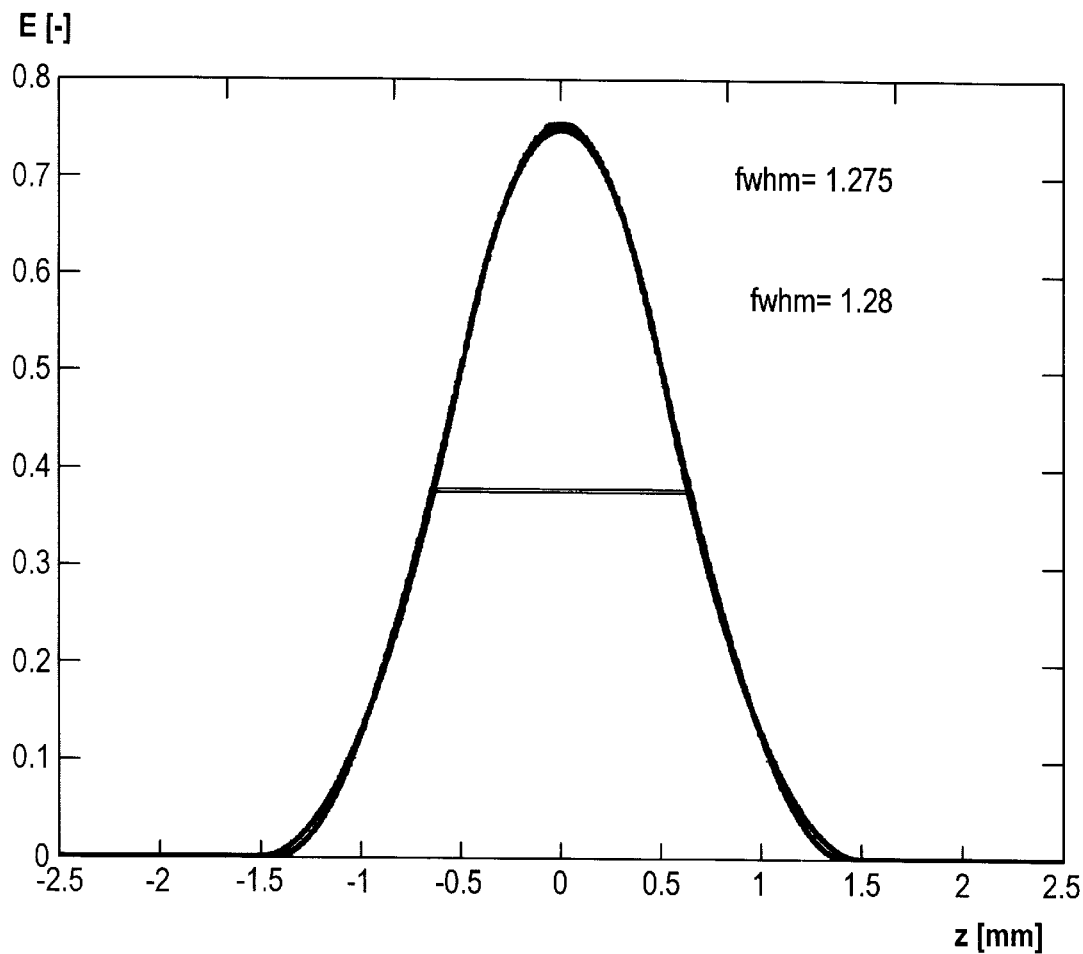
FIG. 5 shows the slice sensitivity profile for two different pitch values that can be achieved with a CT apparatus having a five-line detector that operates according to the inventive method.

As an example, FIG. 5 shows two slice sensitivity profiles calculated with linear weighting g( ) according to equation (1) for spiral scans implemented with a five-line detector, one with pitch p=3, the other with pitch p=7. The two slice sensitivity profiles are the same in the framework of the presentation precision. The measured signal caused by a subject having a defined attenuation value is entered in the slice sensitivity profile as a dimensionless quantity E over the z-direction, with z=0 corresponding to the position of the image plane in the z-direction.

Figure 4:
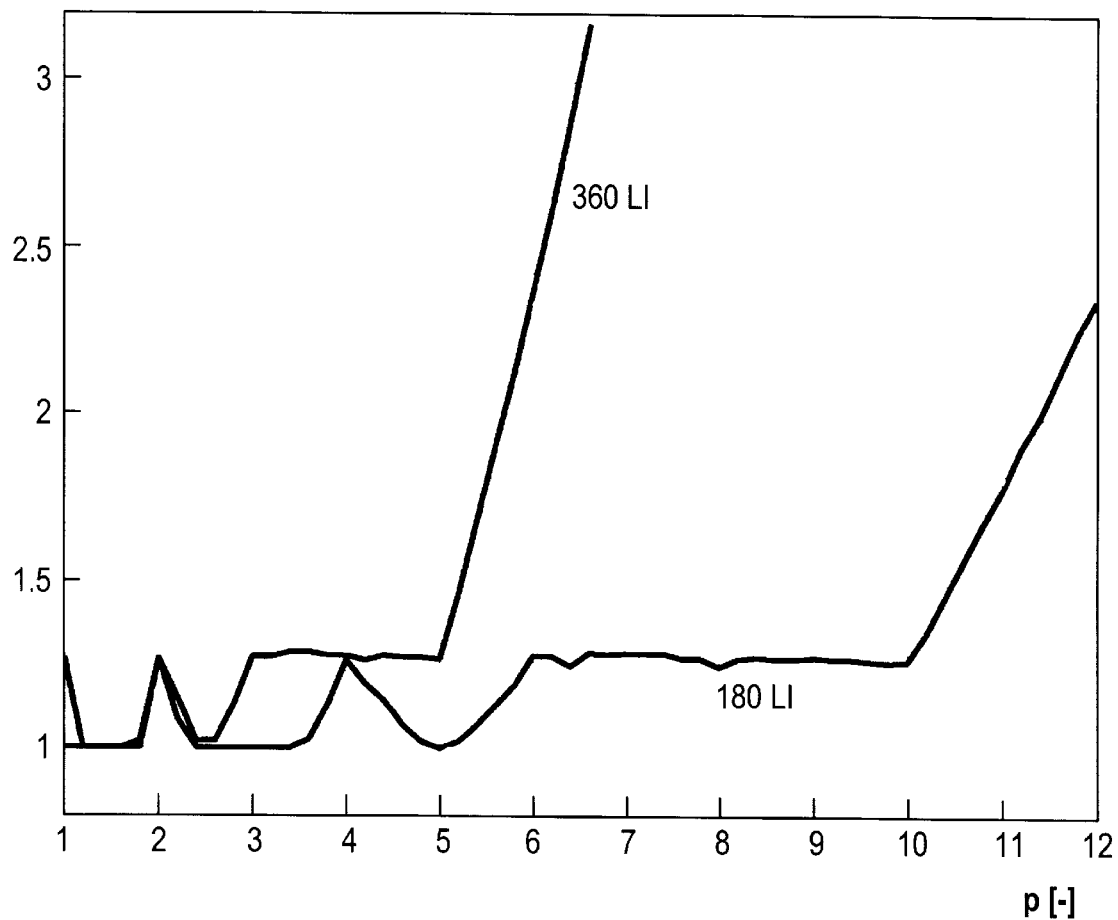
FIG. 4, as described above, shows analogous to FIG. 3, the corresponding diagram for a CT apparatus with five-line detector for the two interpolation methods according to FIG. 2.
Figure 6:
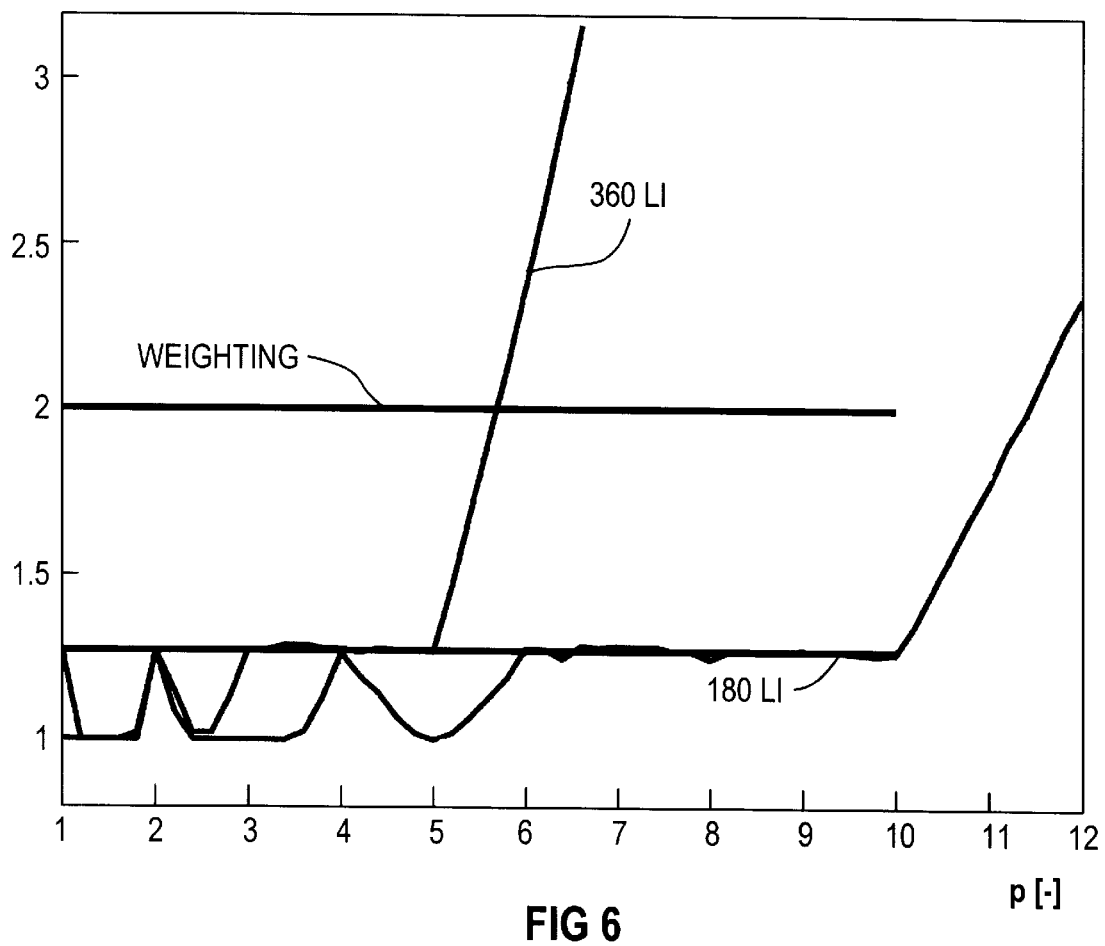
FIG. 6 shows the diagram of FIG. 4 in which two pitch-independent slice thicknesses that can be realized with the inventive method are additionally entered.

Two possible pitch-independent full wave at half maximum, namely FWHM=1.27$d_{coll}$ and FWHM=2$d_{coll}$, are entered in FIG. 6 for spiral scans implemented with a five-line detector, in addition to the illustration already shown in FIG. 4 ($d_{coll}$ is the collimated slice thickness for a detector line set with suitable diaphragms and/or collimators in a known way, and is defined by the geometry of the detector 5).

Figure 7:
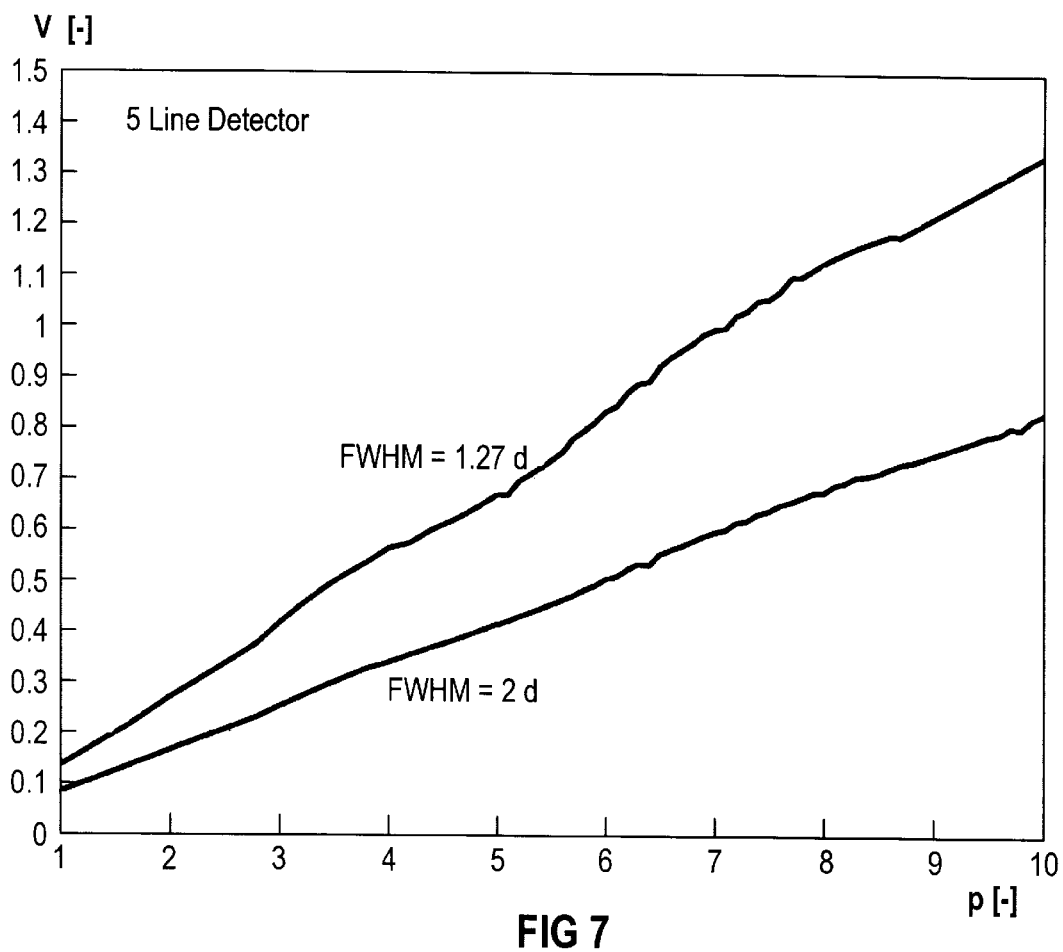
FIG. 7 shows the variance of the pixel noise given constant mA value as a function of the pitch for two different, pitch-independent slice thicknesses for a CT apparatus having a five-line detector and working according to the inventive method.

As a result of the effective slice thickness that is independent of the pitch in the invention, the pixel noise is dependent on the pitch p given a fixed output power of the x-ray source 1, differing from a conventional interpolation. The pixel noise also decreases with decreasing pitch p since lower measured values fall into the z-range ($z_{ima}$−$z_{max}$, $z_{ima}$+$z_{max}$) and contribute to the image due to the weighting. This is schematically shown in FIG. 7 with spiral scans implemented with a five-line detector. The relative variance V of the pixel noise is entered as function of the pitch p given constant output power of the x-ray tube (constant mA value). The variance V is scaled such in FIG. 7 such that the variance V=4/3 is obtained, which would occur in a spiral scan with a single-line detector with 180LI interpolation given the same collimated slice thickness and same tube power.

The two curves are calculated for in FWHM=1.27$d_{coll}$ and FWHM=2$d_{coll}$. For FWHM-1.27$d_{coll}$, the variance given application of the inventive method decreases from V=4/3 at the pitch p=2N to V=1/N.2/3 at the pitch p=1. This corresponds to the N-times dose accumulation compared to a spiral scan with a single-line detector with 360LI interpolation. Keeping the same output power of the x-ray source 1, the applied dose (mAs product) thus can be increased with decreasing pitch p or the output power of the x-ray source 1 can be reduced corresponding to FIG. 7 and the same dose retained, independently of the pitch p.

The inventive method is suitable for a CT apparatus having a single-line or having a multi-line detector. Since a desired, effective slice thickness can be set independently of the pitch p, the operation of an inventive CT apparatus is substantially simplified, since the pitch p is no longer a parameter that defines the resolution in the z-direction. On the contrary, the physician can set the desired, effective slice thickness $d_{eff}$ with the keyboard 12, or more precisely stated can set the desired full wave at half maximum of the slice sensitivity profile, and nonetheless can freely select the pitch p.

Moreover, the physician can enter an effective mA value with the keyboard 12, i.e. an effective output power of the x-ray source 1, such as he or she would select based on his or her experience given a CT apparatus with a single-line detector and the same slice thickness. Dependent on the pitch p, the computer 8 then calculates the output power of the x-ray source 1 that is actually to be set, i.e. an actual mA value, for example according to a curve corresponding to FIG. 7, so that the same pixel noise as in an image acquired with the CT apparatus having a single-line detector will always occur independently of the pitch p.

The weighting function provided in the described exemplary embodiment, which enables setting of the effective slice width $d_{eff}$ independently of the pitch p, is only an example. Other weighting functions that produce different functional relationships between the pitch p and the effective layer thickness $d_{eff}$ can be employed within the framework of the invention. Thus, for example, a weighting function can be provided in addition to the weighting function described in detail or instead of this weighting function, wherein the functional relationship between pitch p and effective slice thickness $d_{eff}$ is that the effective slice thickness $d_{eff}$ is directly proportional to the pitch p.

The described exemplary embodiment is a matter of a CT apparatus of the third generation. A CT apparatus of the fourth generation, which has a stationary, annular detector instead of an arcuate detector rotating together with the x-ray source, can also be operated according to the inventive method and can be inventively constructed.

The present invention can be utilized in medical and non-medical applications.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for reconstructing an image of a slice of an examination subject, said slice having a slice thickness with respect to an image plane, using a spiral scan computed tomography apparatus having an x-ray source which emits an x-ray beam and a radiation detector, comprising at least one line of detector elements, said x-ray beam rotating around an examination subject with a relative longitudinal shift between the x-ray source and the detector occurring with respect to the examination subject during each revolution, said radiation detector producing measured values respectively allocated to one of a plurality of projection angles α and to a z position on a longitudinal axis of the spiral scan, adhering to a constant, dimensionless pitch p during the spiral scan, said pitch being the ratio of said relative shift and a width in the longitudinal direction of a line of said radiation detector, said method comprising the steps of:

- for each projection angle, defining a set of measured values allocated to the projection angle which lie within a maximum distance from the image plane;
- weighting the measured values in said set using a weighting function dependent on the respective spatial distances, in the direction of the longitudinal axis of the spiral scan, of the measured values from the image plane;
- selecting said weighting function to produce a selected, functionally defined relationship between an effective slice thickness, defined by said maximum distance, and said pitch; and
- reconstructing an image of a slice having said effective slice thickness from said measured values.

2. A method as claimed in claim 1 comprising selecting said weighting function so that said functionally defined relationship is that the slice thickness is substantially independent of the pitch.

3. A method as claimed in claim 1 comprising the additional step of operating said x-ray source at an x-ray source power, to obtain said measured values, dependent on the pitch so that pixel noise in said radiation detector is substantially independent of the pitch.

4. A method as claimed in claim 1 wherein said weighting function has a width and comprising the additional step of modifying a width of said weighting function dependent on said pitch for setting said effective slice thickness.

5. A computed tomography apparatus which produces an image of a slice of an examination subject, said slice having a slice thickness with respect to an image plane, comprising:

- an x-ray source which emits an x-ray beam and a radiation detector, comprising at least one line of detector elements, for conducting a spiral scan of an examination subject by rotating said x-ray beam around the examination subject with a relative longitudinal shift between the x-ray source and the detector occurring with respect to the examination subject during each revolution, said radiation detector producing measured values respectively allocated to one of a plurality of projection angles α and to a z position on a longitudinal axis of the spiral scan, while adhering to a constant, dimensionless pitch p during the spiral scan, said pitch being the ratio of said relative shift and a width in the longitudinal direction of a line of said radiation detector; and
- computer means for, for each projection angle, defining a set of measured values allocated to the projection angle which lie within a maximum distance from the image plane, and for weighting the measured values in said set, to obtain a set of weighted measured values, using a weighting function dependent on the respective spatial distances, in the direction of the longitudinal axis of the spiral scan, of the measured values from the image plane, said weighting function being selected to produce a selected, functionally defined relationship between an effective slice thickness, defined by said maximum distance, and said pitch, and said computer means using said set of weighted measured values to reconstruct an image of a slice having said effective slice thickness.

6. A computed tomography apparatus as claimed in claim 5 wherein said x-ray source operates at an actual mA value which produces pixel noise in said image, and said apparatus further comprising means for setting an effective mA value for said x-ray source to cause said x-ray source to operate at an actual mA value which produces pixel noise in said image corresponding to pixel noise which would occur in an image having a slice thickness acquired using a detector with a single line of detector elements.

* * * * *